United States Patent [19]
Chen

[11] Patent Number: 5,904,826
[45] Date of Patent: May 18, 1999

[54] COMPARTMENTAL DEVICE FOR HIGH SPEED SUBMARINE GEL ELECTROPHORESIS

[76] Inventor: Stephen L. Chen, 18510 SW. Honeywood Dr., Aloha, Oreg. 97006

[21] Appl. No.: 09/135,461

[22] Filed: Aug. 17, 1998

[51] Int. Cl.⁶ ................................................. G01N 27/26
[52] U.S. Cl. ........................ 204/616; 204/618; 204/621
[58] Field of Search .................................. 204/606, 616, 204/618, 621

[56] References Cited

U.S. PATENT DOCUMENTS

| | | | |
|---|---|---|---|
| 4,702,814 | 10/1987 | Audeh | 204/299 R |
| 5,074,981 | 12/1991 | Fairfield | 204/182.8 |
| 5,149,418 | 9/1992 | Flesher | 204/299 R |
| 5,549,806 | 8/1996 | Chen | 204/621 |
| 5,709,788 | 1/1998 | Chen | 204/619 |

OTHER PUBLICATIONS

Products Catatog (1994) of Hoefer Scientific Instruments, p. 30 654 Minnesota St. Box 77387, San Francisco, CA 94107.

*Primary Examiner*—David A. Redding

[57] ABSTRACT

An improvement in submarine gel electrophoresis apparatus is provided for performing electrophoresis at elevated voltages. A compartmental device is introduced into a conventional submarine gel apparatus to compartmentalize a buffer so that the buffer functions as a potent coolant but without generating massive heat during electrophoresis, which enables the submarine gel electrophoresis to be performed at higher voltages.

6 Claims, 3 Drawing Sheets

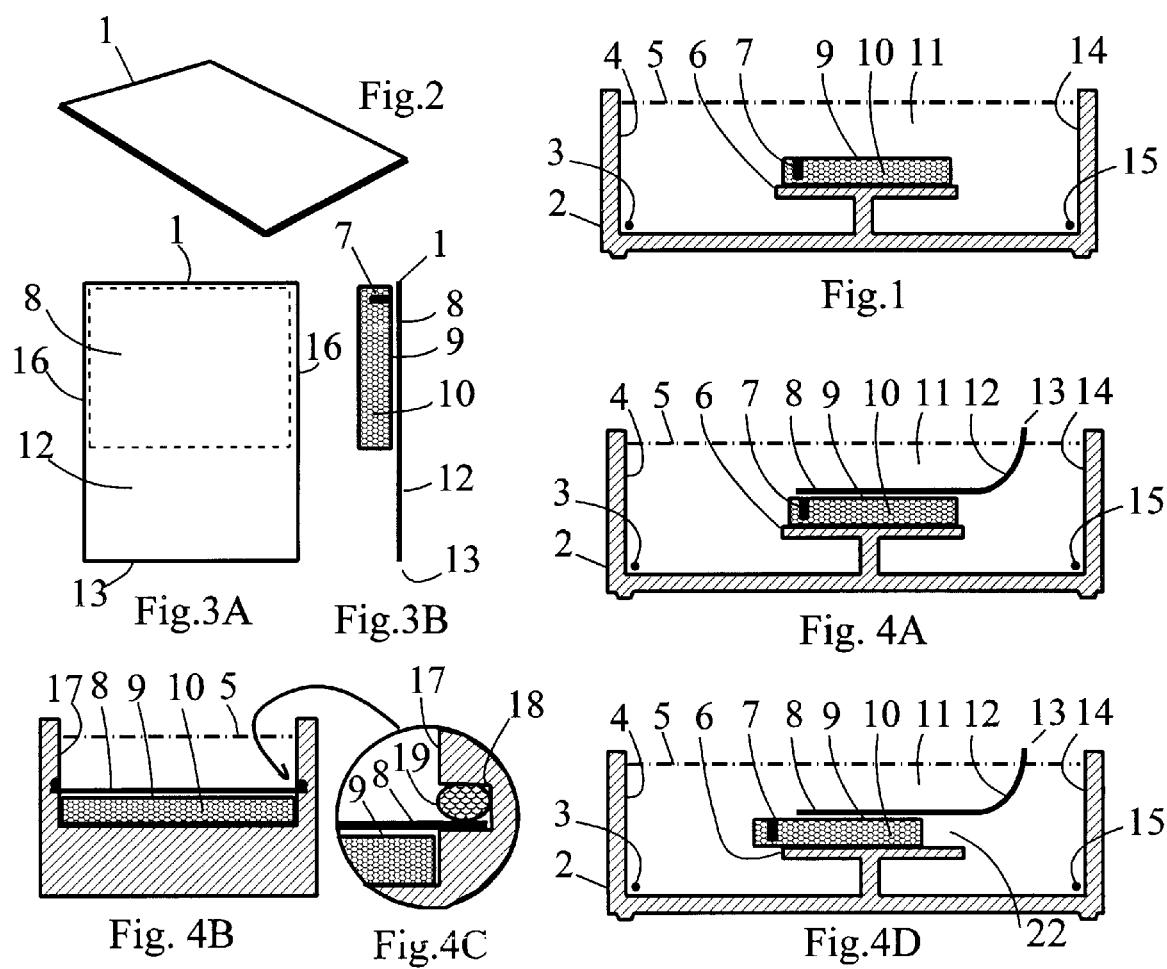

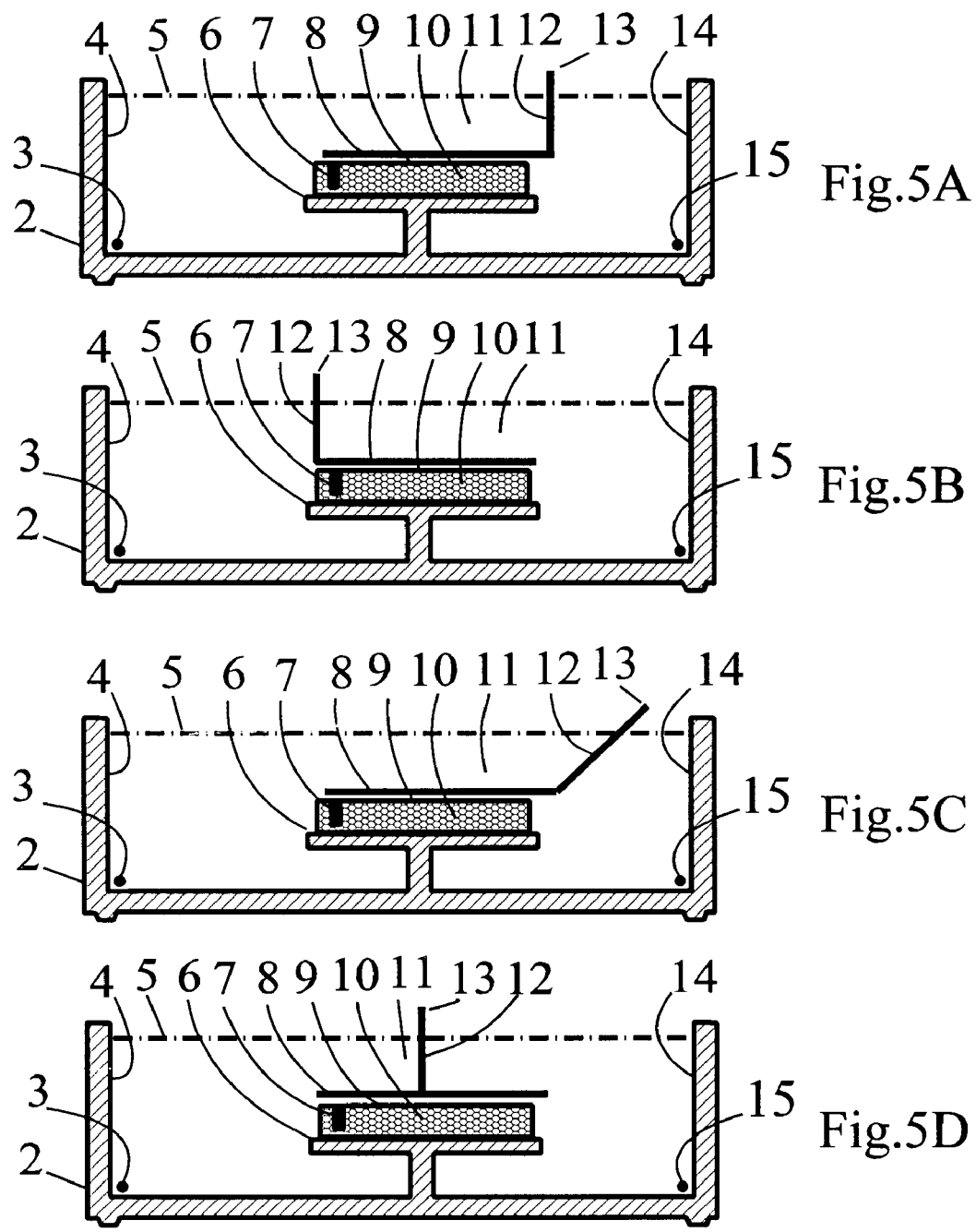

COMPARTMENTAL DEVICE FOR HIGH SPEED SUBMARINE GEL ELECTROPHORESIS

BACKGROUND OF THE INVENTION

1. Field of The Invention

The present invention is generally related to devices in submarine gel electrophoresis and is particularly directed to improvements of conventional submarine gel apparatus for decreasing temperature in gel matrix so that higher voltage can be applied in electrophoresis.

2. Description of the Prior Arts

Gel electrophoresis is one of the most commonly utilized tools in biomedical researches and industries. In gel electrophoresis, a sample of mixed biomolecules is applied into sample wells of a gel matrix, a buffer conducts an electric field from a pair of electrodes to the gel matrix, and the components in the sample migrate across the gel matrix. Different components migrate at different speed so that they can be separated from each other in electrophoresis. The migration rate is directly related to the voltage of the electric field applied. Higher voltage generates higher migration rate under given condition.

Agarose gel is one of the most popularly used gel matrix. An agarose gel matrix is formed from an agarose gel solution by a decrease of temperature. The formed agarose gel matrix is readily reversible to solution format whenever the temperature rises to a certain point. The properties of agarose gel matrix are significantly altered when the temperature changes due to the nature of the gel forming mechanism. Thus, it is critical for agarose gel electrophoresis to maintain the gel matrix at low temperature.

Conventional submarine gel electrophoresis is the most commonly used format for agarose gel due to its simplicity in manipulation. The gel matrix is usually immersed completely in a buffer. A typical feature of this format is that electric current travels from one electrode to another electrode via both a gel pathway through the gel matrix and a buffer pathway through the buffer around the gel matrix. The electric current in buffer pathway has no function for the migration of samples but generates unwanted massive heat, which severely prevents heat transfer from the gel matrix to the buffer. The voltage applied to submarine gel electrophoresis is, therefore, limited within low level range in order to maintain the gel matrix at low temperature.

The existence of a buffer pathway around gel matrix results in disadvantages:

(1) The electrophoresis has to be a slow process because the voltage applied must be limited within low level range to avoid generating excess heat which will otherwise distort the gel matrix.

(2) A strong buffering capacity is required for maintaining PH balance under the heavy electric current condition.

These disadvantages are long-felt problems. Attempts have been made for pursuing improvement of the conventional submarine gel electrophoresis.

Audeh, U.S. Pat. No. 4,702,814, teaches a submarine gel device having a gas collecting means and a conduit for eliminating the requirement of having a strong buffering capacity in buffer system. But Audeh fails to recognize the basis of the requirement. A buffer pathway is inherited in his device. Thus, Audeh fails to accelerated the slow process of electrophoresis.

Hoefer, 1994 Catalog of Hoefer Scientific Instruments at page 30, teaches a submarine gel device having a coolant mixture in base chamber for accelerating the slow process of electrophoresis. Hoefer, However, also fails to recognize the basis of those disadvantages. A buffer pathway is still inherited in his device, which indicates that his acceleration is only a limited improvement.

Fairfield, U.S. Pat. No. 5,074,981, teaches a device for high speed gel electrophoresis. Fairfield recognizes the basis of those disadvantages so that the buffer pathway is removed from his device. But, Fairfield fails to find a correct solution to establish his improvement. To reach his high speed, Fairfield sacrifices the most attractive advantage of submarine gel electrophoresis, the simplicity, and replaces it with a series of delicate requirements, a series of complicate manipulations, a series of time-consuming steps, and a series of risk of failure. The extra time required for operating his device is much longer than the time saved by his device. Fairfield's device is, therefore, practically infeasible for most routine applications.

Chen, U.S. Pat. No. 5,549,806, teaches a device to reach high speed submarine gel electrophoresis. Chen has recognized the basis of those disadvantages and achieved his high speed with a simple strategy, using water to replace buffer. Chen's device, however, generates new concerns and limitations:

(1) The buffer is frequently disposed after each electrophoresis because it requires extra labor to separate buffer from water after electrophoresis. The buffer should be, otherwise, reusable for several times due to the elimination of the buffer pathway in Chen's device. The buffer reuse has extraordinary meaning for environment protection because there are usually some extremely hazard chemicals, such as Ethidium Bromide, mixed in the buffer.

(2) In practice, electrophoresis may be, sometimes, stopped halfway for a brief view or manipulation of the gel matrix and then resumed to completion. A new buffer, in this case, is needed to add to the device, which generates more waste and extra operations.

A device being able to reach high speed in submarine gel electrophoresis but without negative impact at other aspects remains unsolved and is highly desirable.

SUMMARY OF THE INVENTION

It is, therefore, an object of the present invention to provide a device with user and environmental friendly features in pursuing high speed submarine gel electrophoresis. The advantages of the present invention are:

1. It provides the capacity of using the same buffer many times, the buffer life time in the present invention is significantly longer than that in conventional submarine gel devices, which is a meaningful contribution for environment protection.

2. It provides the convenience of gel viewing and manipulation during electrophoresis without buffer change, which reduces buffer waste and user's operation.

BRIEF DESCRIPTION OF THE DRAWINGS

FIG. 1 is a longitudinal side-view of a conventional submarine gel apparatus to be improved.

FIG. 2 is a perspective view of a first embodiment of the compartmental device used for converting the conventional apparatus in FIG. 1 into a high speed apparatus.

FIG. 3A and 3B demonstrate a dimensional relation between the compartmental device from FIG. 2 and the gel matrix from FIG. 1.

FIG. 4A, B, C, and D demonstrate the installation of the first embodiment.

FIG. 5A, B, C, and D demonstrate some minor variations of the first embodiment.

DETAIL DESCRIPTION OF THE INVENTION

Figure 6A:
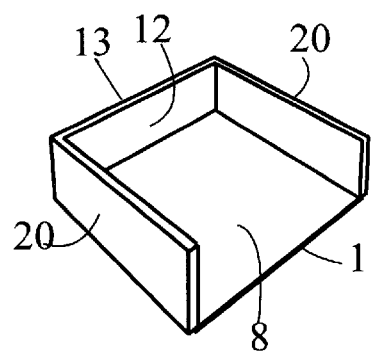
FIG. 6A, B, C, D, and F demonstrate a removable embodiment of the improvement.
Figure 6C:
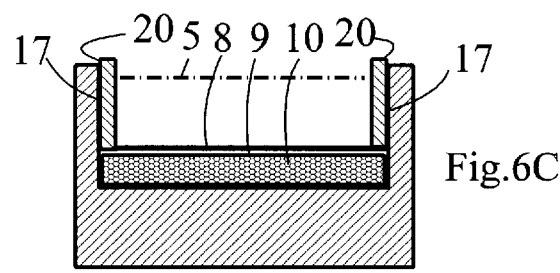

Buffer in submarine gel electrophoresis has two functions, conducting electric current to gel matrix and absorbing heat away from the gel matrix. For the first function, the buffer should have higher conductivity. But for the second function, the buffer should have no conductivity.

The essential idea of the present invention is to compartmentalize the buffer pathway with a thin sheet of plastic so that the electric circuit in the buffer pathway is blocked but the heat absorption from the gel matrix is substantially maintained.

FIG. 1 shows an apparatus 2 for conventional gel electrophoresis viewed from longitudinal side. Gel matrix 10 seats against gel bed 6 between a first buffer chamber 14 and a second buffer chamber 4. Buffer 5 immerses gel matrix 10 completely. A first surface 9 of gel matrix 10 opens to buffer 5. Electric current travels from a first electrode 15 to a second electrode 3 via both gel matrix 10 and buffer 5 around gel matrix 10. This portion of buffer 5 is defined as buffer pathway 11.

FIG. 2 shows a first embodiment of a device 1 for compartmentalizing apparatus 2 from FIG. 1 into a high speed apparatus. In this embodiment, device 1 is a clear thin plastic sheet. The thickness of device 1 should be as thin as possible for heat transfer efficiency. But the rigidity of device 1 should be also balanced at an acceptable level so that an even distribution of electric field across gel matrix 10 can be maintained. A piece of clear polycarbonate sheet at 0.3 mm thickness, for example, gives an proper result. The width of device 1 is determined by the width of gel matrix 10, having about 10 mm extra at each edge for attaching to apparatus 2. The length of device 1 is longer than that of gel matrix 10. A portion of device 1 overlapped with gel matrix 10 is defined as a first portion 8 and the rest of device 1 is defined as a second portion 12, as shown in FIG. 3A and 3B.

Device 1 is anchored to apparatus 2 along its longitudinal side walls 17. A pair of recessive channels 18 is built on interior side of side walls 17 for receiving edges 16 of device 1. Device 1 is installed as replaceable part and fixed in recessive channels 18 by a strip of sponge 19, as shown in FIG. 4C. FIG. 4B is a cross-sectional view of apparatus 2 viewed from one end. FIG. 4C shows an enlarged detail of the joint from FIG. 4B.

First portion 8 of device 1 is placed face to face with gel bed 6, forming a gel compartment 22 for holding gel matrix 10 inbetween. The net space between first portion 8 and gel bed 6 is slightly greater, about I mm, than the thickness of gel matrix 10 so that gel matrix 10 can be moving in and moving out smoothly through gel compartment 22. First surface 9 of gel matrix 10, when placed in gel compartment 22, is very close to first portion 8. The best performance is reached when gel matrix 10 is completely covered by first portion 8. The resolution of samples may be reduced slightly if sample wells 9 are not substantially placed inside gel compartment 22. But it still works when a small portion of gel matrix 10 remains extruding. Gel compartment 22, when gel matrix 10 is placed in, allows buffer 5 to permeate from first buffer chamber 14 to second buffer chamber 4 through gel compartment 22.

Second portion 12 of device 1 extends from first portion 8 and bends into a curve shape for easy installation consideration. Second portion 12 can also be arranged in other shapes and extended from other positions of first portion 8, as shown in FIG. 5A, 5B, 5C, and 5D. But in all cases, an edge 13 of second portion 12 should extend to the point where buffer 5 is substantially sectioned into a dead ended buffer compartments.

Buffer pathway 11, in the compartmentalized apparatus, is now substantially sectioned into a dead ended compartment by first portion 8, second portion 12, and side walls 17. Buffer 5 in this dead ended buffer compartment loses its electric circuit so that it generates no heat during electrophoresis but functions only as a coolant. In this case, the surface level of buffer 5 can be elevated for enhancing its cooling power without causing high electric current, which is, otherwise, a critical limitation in conventional apparatuses.

Electrophoresis in the compartmentalized apparatus is performed as follows:

1. Have the compartmentalized apparatus with buffer 5 filled.
2. Place gel matrix 10 partially into gel compartment 22 between first portion 8 and gel bed 6, as shown in FIG. 4D.
3. Load samples into sample wells 7.
4. Push gel matrix 10 further in until most of gel matrix 10 are covered by first portion 8, as shown in FIG. 4A.
5. Perform electrophoresis at higher voltage, usually about double scale, for a shorten time.

Gel matrix 10 may be, if desired, removed for a brief view or manipulation and then placed back for a continuation of electrophoresis.

Figure 6B:
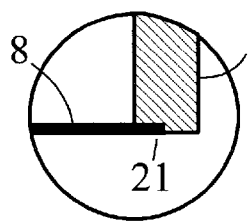

FIG. 6A through 6F demonstrate a removable embodiment of the present invention. In FIG. 6A, device 1 joints to two side pieces 20, instead of jointing to side walls 17 in the first embodiment. Second portion 12 of device 1 is thicken and jointed to two side pieces 20 to form a firm rigid frame. First portion 8 remains as a thin sheet and is taped to side pieces 20 with a clear water-proof tape 21, as shown in FIG. 6B.

To meet the essential idea of the invention, buffer compartment, the outside width between two side pieces 20 should match the inside width between two side walls 17 as close as possible but the whole removable unit should be able to be placed and removed smoothly. A total of 0.5 mm difference between the two widths gives a smooth movement and the buffer leakage between side pieces 20 and side walls 17 is still negligible.

The distance between first portion 8 and gel bed 6 is now the same as the thickness of gel matrix 10 because there is not horizontal movement of gel matrix 10.

Figure 6D:
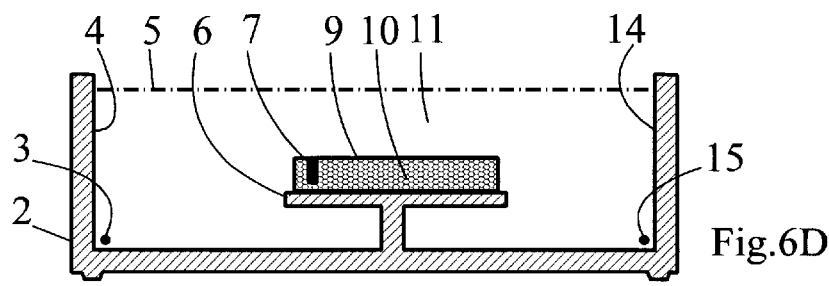
Figure 6F:
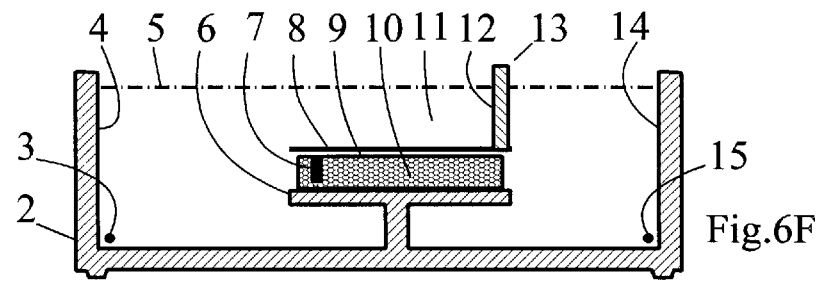

Electrophoresis with the removable unit is performed as follows:

1. Have conventional apparatus 2 with buffer 5 filled.
2. Place gel matrix 10 on gel bed 6 and load samples into sample wells 7, as shown in FIG. 6D.
3. Place the removable unit on top of gel matrix 10, as shown in FIG. 6F.
4. Electrophoresis at higher voltage for a shorten time.

Although the description above contains specifications, it will apparent to those skilled in the art that a number of other variations and modifications may be made in this invention without departing from its spirit and scope. A strip of sponge 19, for example, can be omitted from the first embodiment and replaced with a tape for anchoring device 1, device 1 can be other kinds of material and thicker than 0.3 mm, and the length of gel matrix 10 can be longer than the length of first portion 12. Thus, the description as set out above should not be constructed as limiting the scope of the invention but as merely providing illustration of some of the presently preferred embodiments of the invention.

What is claimed is:

1. In a submarine gel electrophoresis apparatus including a first electrode in a first buffer chamber, a second electrode in a second buffer chamber, a gel matrix seated against a gel bed between said first and second buffer chambers, and a buffer immersing said gel matrix and conducting an electric current from said first electrode to said second electrode via both said gel matrix and a buffer pathway through said buffer above said gel matrix, said gel matrix having a first surface facing said buffer, the improvement comprising;

a compartmental device introduced into said submarine gel electrophoresis apparatus for suppressing electric current, a first portion of said compartmental device, having at least a sheet structure in a size dimension matching substantially to the size dimension of said gel matrix and a thickness enabling a substantial portion of heat generated in said gel matrix to be transferred across said sheet structure into said buffer during electrophoresis, placed adjacent to said first surface of said gel matrix, covering a substantial portion of said first surface of said gel matrix, and allowing a permeation of said buffer from said first buffer chamber to said second buffer chamber via a space between said first portion of said compartmental device and said first surface of said gel matrix, and a second portion of said compartmental device extending from said first portion, sectioning said buffer pathway substantially into a dead ended buffer compartment defined by said first portion, said second portion, and side walls of said submarine gel electrophoresis apparatus.

2. The compartmental device of claim 1 wherein said sheet structure of said first portion is a thin sheet at 0.3 mm thickness.

3. The compartmental device of claim 1 wherein said first portion is postioned away from said gel bed at a distance 1 mm greater than the thickness of said gel matrix.

4. In a submarine gel electrophoresis apparatus including a first electrode in a first buffer chamber, a second electrode in a second buffer chamber, a gel matrix seated against a gel bed between said first and second buffer chambers, and a buffer immersing said gel matrix and conducting an electric current from said first electrode to said second electrode via both said gel matrix and a buffer pathway through said buffer above said gel matrix, said gel matrix having a first surface facing said buffer, the improvement comprising;

a compartmental device introduced into said submarine gel electrophoresis apparatus for suppressing electric current, a first portion of said compartmental device, having at least a thin sheet structure in a thickness enabling at least 50% of the heat generated in said gel matrix to be transferred across said thin sheet structure into said buffer during electrophoresis time period and in a size dimension corresponding substantially to the size dimension of said first surface of said gel matrix, placed face to face with said first surface of said gel matrix, covering at least a substantial portion of said first surface of said gel matrix and permitting a permeation of said buffer from said first buffer chamber to said second buffer chamber via a gap between said first portion of said compartmental device and said first surface of said gel matrix, and a second portion of said compartmental device extending from said first portion, sectioning said buffer pathway substantially into a dead ended buffer compartment defined by said first portion, said second portion, and side walls of said submarine gel electrophoresis apparatus.

5. The compartmental device of claim 4 wherein said thin sheet structure of said first portion is a polycarbonate sheet.

6. The compartmental device of claim 4 wherein said thin sheet structure of said first portion is a polycarbonate sheet at a thickness of 0.3 mm.

* * * * *